United States Patent
Auerbach-Nevo et al.

(10) Patent No.: US 11,857,564 B2
(45) Date of Patent: Jan. 2, 2024

(54) HEMOSTATIC COMPOSITION COMPRISING AN ANION EXCHANGER AND A CALCIUM SALT

(71) Applicant: Omrix Biopharmaceuticals Ltd., Rehovot (IL)

(72) Inventors: Tamar Auerbach-Nevo, Rehovot (IL); Tali Negreanu-Gilboa, Givatayim (IL); Hadas Alperin, Ramat-Gan (IL); Israel Nur, Nes-Ziona (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 181 days.

(21) Appl. No.: 15/840,329

(22) Filed: Dec. 13, 2017

(65) Prior Publication Data

US 2018/0177818 A1 Jun. 28, 2018

Related U.S. Application Data

(60) Provisional application No. 62/437,840, filed on Dec. 22, 2016.

(30) Foreign Application Priority Data

Dec. 22, 2016 (IL) .......................................... 249725

(51) Int. Cl.
| | | |
|---|---|---|
| *A61K 31/721* | (2006.01) | |
| *A61K 33/06* | (2006.01) | |
| *A61P 7/04* | (2006.01) | |
| *A61L 26/00* | (2006.01) | |
| *A61L 15/18* | (2006.01) | |
| *A61K 33/14* | (2006.01) | |

(52) U.S. Cl.
CPC ............ *A61K 31/721* (2013.01); *A61K 33/06* (2013.01); *A61K 33/14* (2013.01); *A61L 15/18* (2013.01); *A61L 26/0004* (2013.01); *A61P 7/04* (2018.01); *A61L 2300/208* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | | |
|---|---|---|---|---|
| 5,502,042 | A * | 3/1996 | Gruskin | .............. A61L 26/0023 |
| | | | | 514/54 |
| 7,923,031 | B2 | 4/2011 | Moeller | |
| 8,110,208 | B1 * | 2/2012 | Hen | ...................... A61L 15/225 |
| | | | | 424/422 |
| 8,741,335 | B2 | 6/2014 | McCarthy | |
| 2009/0062849 | A1 | 3/2009 | Dowling et al. | |
| 2017/0266339 | A1 * | 9/2017 | Landolina | .............. A61L 24/001 |

FOREIGN PATENT DOCUMENTS

| | | |
|---|---|---|
| CN | 103025360 A | 4/2013 |
| RU | 2006131128 A | 3/2008 |
| WO | WO 1989/004657 | 6/1989 |
| WO | WO 1993/005822 | 4/1993 |
| WO | WO 1999/056798 | 11/1999 |
| WO | 2008076598 A1 | 6/2008 |
| WO | WO 2012/087774 | 6/2012 |
| WO | WO 2013/071235 | 5/2013 |

OTHER PUBLICATIONS

Holcomb JB, Pusateri AE, Harris RA, et al. (Effect of dry fibrin sealant dressings versus gauze packing on blood loss in grade V liver injuries in resuscitated swine. J Trauma. 1999; 46:49-58).

International Search Report re: PCY/IL2017/000009 dated Apr. 6, 2018.

Gao, Polymer Science in Pharmaceutics, Edited by Gao Feng, East China University of Science and Technology Press, pp. 1-3 (English language translation is being obtained. It will be forwarded as soon as it is completed).

Huang Ping, Operating Room Nursing Technical Guidance, Yunnaan Science and Technology Press, pp. 1-3(English language translation is being obtained. It will be forwarded as soon as it is completed).

Bjorses, et al., In vitro and in vivo Evaluation of Chemicall Modified Degradable Starch Microspheres for Topical Haemostasis, Acta Biomaterialia, 2011, pp. 2558-2565, vol. 7.

* cited by examiner

*Primary Examiner* — David J Blanchard
*Assistant Examiner* — Daniel F Coughlin
(74) *Attorney, Agent, or Firm* — David R. Crichton

(57) ABSTRACT

Provided are pharmaceutical compositions comprising an anion exchanger and a calcium salt; methods for inducing hemostasis at a site of bleeding by applying to the site of bleeding an effective amount of the compositions; and methods of preparation of the compositions.

5 Claims, 3 Drawing Sheets

HEMOSTATIC COMPOSITION COMPRISING AN ANION EXCHANGER AND A CALCIUM SALT

FIELD OF THE INVENTION

The invention relates to the field of hemostatic compositions. More particularly, the invention relates to hemostatic compositions comprising an anion exchanger and calcium; and methods of use thereof.

BACKGROUND OF THE INVENTION

Bleeding is the term commonly used to describe the escape of blood from the circulatory system of a vertebrate. Bleeding may occur inside the body (internal bleeding) or outside the body (external bleeding). The site of bleeding can be almost any area of the body. Typically, internal bleeding occurs when blood leaks out through damage to a blood vessel or organ. External bleeding occurs either when blood exits through a break in the skin, or when blood exits through a natural opening in the body, such as the mouth, nose, ear, vagina, or rectum.

Bleeding may be caused by a wide variety of incidents or conditions, including traumatic injury (including abrasions, grazes, lacerations, incisions, puncture wounds from items such as a needle or a knife, crushing injuries and gunshot wounds) or certain medical conditions, such as those associated coagulations compromised subjects which have deficiencies of coagulation factors. Additionally, bleeding may be caused by use of certain medicaments, such as some non-steroidal anti-inflammatory drugs (NSAIDs) or anti-coagulation drugs e.g. warfarin, low molecular weight heparin, Apixaban (ELIQUIS®), Dabigatran (PRADAXA®), Edoxaban (SAVAYSA®) and Rivaroxaban (XARELTO®).

Continued, untreated bleeding may result in exsanguination, i.e., excessive decrease of blood volume (hypovolemia), leading to death.

The stopping or controlling of bleeding is referred to as hemostasis, which involves blood coagulation, and promoting, accelerating or enhancing this mechanism, is an important part of both, first aid and surgery. Agents and compositions which enhance, promote or accelerate hemostasis are referred to as "hemostatic agents".

Hemostatic agents may comprise hemostats, sealants or adhesives. Typically, hemostats are subdivided into mechanical hemostats (gelatin, collagen, oxidized regenerated cellulose, etc.), active hemostats (such as thrombin), flowable hemostats (such as gelatin matrices in conjunction with thrombin), and fibrin sealants.

Some known hemostats require lengthy preparation prior to use, involving numerous steps, which waste valuable time in emergency situations.

Biological hemostats are very effective, yet they carry a potential safety risk and their production costs are high Many known hemostats require refrigeration, which may be unavailable or very costly in developing countries, as well as in various situations (including in battle fields, in isolated areas, in emergency situations) or during electricity failures. Furthermore, the requirement for refrigeration increases costs of production, shipment and storage.

Many known hemostats are ineffective for patients who are using blood-thinning medications, such as heparin, Aspirin or Coumadin.

Many known hemostats include procoagulants, which carry a potential risk of contamination, have high production costs, short expiration time and usually require refrigeration.

There is thus a need for a safe and effective hemostat, which is devoid of at least some of the disadvantages of the prior art.

Background art includes U.S. Pat. Nos. 5,502,042 and 8,741,335; US Publication No. 2009/0062849; and PCT Publication Nos. WO 2013/071235 and 1993/05822.

SUMMARY OF THE INVENTION

The present invention provides a hemostatic composition comprising an anion exchanger; calcium and a pharmaceutically acceptable carrier, as well as methods of use thereof for inducing hemostasis.

According to an aspect of some embodiments of the present invention, there is provided a method for inducing hemostasis at a site of bleeding in a subject in need thereof, the method comprising applying to the site of bleeding an effective amount of a hemostatic composition comprising an anion exchanger and a calcium salt.

According to some embodiments, the anion exchanger comprises one or more positively-charged groups bound to a matrix.

According to some embodiments, the positively-charged groups (also referred to as polycations) are provided by a base selected from the group consisting of a strong base, a weak base and a combination thereof.

According to some embodiments, the strong base comprises quaternary amino groups.

According to some embodiments, the weak base comprises an amino group selected from the group consisting of a primary amino group, a secondary amino group, a tertiary amino group and a combination thereof.

According to some embodiments, the weak base consists of Diethylaminoethyl (DEAE) groups.

According to some embodiments, the matrix is selected from the group consisting of an aliphatic polyester, a polysaccharide, a polypeptide, polystyrene-divinylbenzene, a protein (such as collagen gelatin or albumin), silica and a combination thereof.

According to some embodiments, the matrix is cross-linked, optionally covalently cross-linked.

According to some embodiments, the composition is substantially devoid of any protein of the blood clotting cascade.

According to some embodiments, the composition is in a form selected from the group consisting of a slurry, powder, fiber, film, patch and liquid.

According to some embodiments, wherein the composition in the form of slurry or liquid, the composition further comprises a pharmaceutically acceptable carrier.

According to some embodiments, applying is carried out by applying pressure on the composition, optionally towards the site of bleeding.

According to an aspect of some embodiments of the present invention, there is provided a hemostatic composition comprising an anion exchanger; a calcium salt; and optionally, a pharmaceutically acceptable carrier.

According to some embodiments, the anion exchanger comprises one or more positively-charged groups bound to a matrix.

According to some embodiments, the anion exchanger is linked to a solid phase.

According to some embodiments, the positively-charged groups consist of a base selected from the group consisting of a strong base, a weak base and a combination thereof.

According to some embodiments, the strong base comprises quaternary amino groups.

According to some embodiments, the weak base comprises an amino group selected from the group consisting of a primary amino group, a secondary amino group, a tertiary amino group and a combination thereof.

According to some embodiments, the weak base consists of Diethylaminoethyl (DEAE) groups.

According to some embodiments, the matrix is selected from the group consisting of an aliphatic polyester, a polysaccharide, a polypeptide, polystyrene-divinylbenzene, silica and a combination thereof.

According to some embodiments, the matrix is cross-linked, optionally covalently cross-linked.

According to some embodiments, the polysaccharide is selected from the group consisting of cellulose, dextran, agarose, and combinations thereof.

According to some embodiments, the protein is a structural protein such as collagen or gelatin, or proteins having high abundance in blood plasma such as albumin.

According to some embodiments, the composition is substantially devoid of any protein of the blood clotting cascade.

According to some embodiments, the composition is in a form selected from the group consisting of a slurry, powder, film, patch and liquid.

According to some embodiments, the composition in the form of slurry or liquid further comprises a pharmaceutically acceptable carrier.

According to an aspect of some embodiments of the present invention, there is provided a hemostatic composition comprising Diethylaminoethyl (DEAE) bound to a matrix; and a calcium salt.

According to an aspect of some embodiments of the present invention, there is provided a method for the preparation of a hemostatic composition comprising preparing an anion exchanger by covalently binding one or more positively-charged groups to a cross-linked matrix; and adding a calcium salt to said anion exchanger.

According to an aspect of some embodiments of the present invention, there is provided a hemostatic composition obtainable by the method disclosed herein.

As used herein, the term "inducing hemostasis" refers to causing, bringing about, promoting, accelerating and/or enhancing hemostasis.

As used herein, the term "a site of bleeding" refers to a site that is actively bleeding and to a site that may be prone or susceptible to bleeding complications such as for example a surgical site, anastomotic site, and/or suture site.

As used herein, the term "pharmaceutically acceptable carrier" refers to any inert diluent or vehicle which has no biological activity and which is suitable for use in humans or other animals. The carrier may be selected from any of the carriers known in the art such as, but not limited to, phosphate buffered solution (PBS), saline, sodium chloride solution, calcium chloride solution, lactated ringers (LR), 5% dextrose in normal saline, different saccharides, sugar alcohols (such as mannitol, sorbitol) and water for injection.

As used herein, the term "slurry" refers to a thick, soft, moist substance. Typically, a slurry is produced by mixing dry ingredients (e.g. powder or solid hydrophillic particles) with a liquid. The dry ingredients concentration can be 0.5% to 99% w/w of the entire slurry composition. Typically, a slurry is a moldable material in the temperature range of 1.5-40° C.

As used herein, the term "devoid of" with regard to a component of a composition refers to a component which is present in the composition at a concentration of less than 0.1% w/w of the total composition.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein the term "about" refers to ±10%.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
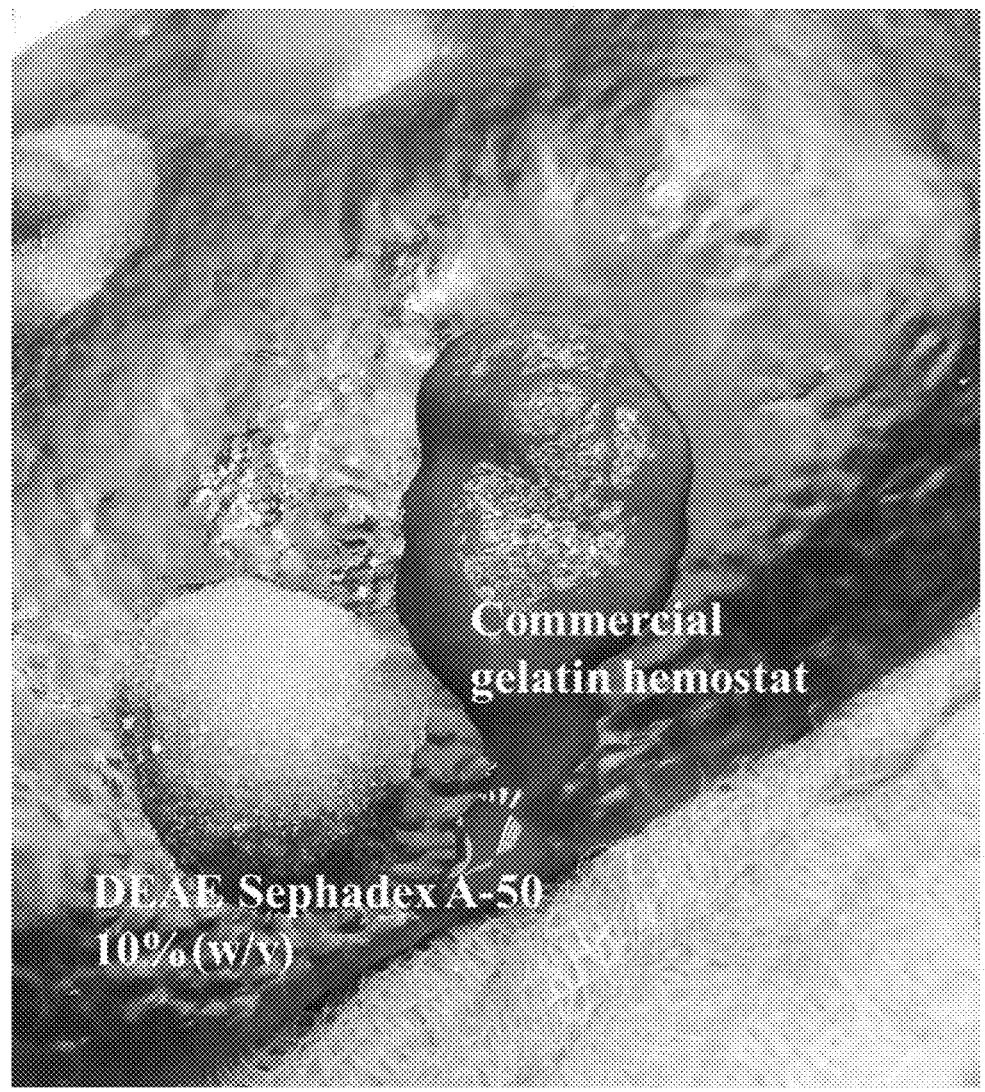
FIG. 1 shows reduction in bleeding in an in-vivo heparinized porcine spleen circular punch model (4 mm diameter/2 mm depth) following application of DEAE SEPHADEX™ A-50 (10% w/v) and a commercial gelatin hemostat, with a compression time of 30 seconds (for DEAE SEPHADEX™ A-50) or 60 seconds (for commercial gelatin hemostat).

The present invention provides a hemostatic composition comprising an anion exchanger; a calcium salt and optionally, a pharmaceutically acceptable carrier, as well as methods of use thereof in achieving hemostasis.

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways.

The phraseology and terminology employed herein are for descriptive purpose and should not be regarded as limiting.

According to an aspect of some embodiments of the present invention, there is provided a method for inducing hemostasis in a subject in need at a site of bleeding, the method comprising applying to the site of bleeding an effective amount of a hemostatic composition comprising an anion exchanger and a calcium salt.

According to an aspect of some embodiments of the present invention, there is provided a hemostatic composition comprising an anion exchanger and a calcium salt for use in inducing, hemostasis at a site of bleeding.

According to an aspect of some embodiments of the present invention, there is provided the use of a hemostatic composition comprising an anion exchanger and a calcium salt in the manufacture of a medicament for inducing hemostasis.

According to an aspect of some embodiments of the present invention, there is provided the use of a hemostatic pharmaceutical composition comprising an anion exchanger and a calcium salt in the manufacture of a medicament for inducing hemostasis.

According to some embodiments of the method, composition for use, use or method of preparation disclosed herein, the anion exchanger comprises one or more positively-charged groups (at a pH between 2 to 10) (also referred to as polycations) bound to a matrix. In some such embodiments, the hemostatic composition is devoid of polyanions.

According to some embodiments of the method, pharmaceutical composition for use, use or method of preparation disclosed herein, the anion exchanger comprises one or more positively-charged groups (at a pH between 2 to 10) (also referred to as polycations) bound to a matrix. In some such embodiments, the hemostatic composition is devoid of polyanions (such as polyanionic polymers).

Polyanions are molecules or chemical complexes having more than one negative charge. Polycations are molecules or chemical complexes having more than one positive charge.

In one embodiment, the matrix may include anionic residues; however, the overall net charge of the anion exchanger will be positive.

According to some embodiments, the positively-charged groups are present in the hemostatic composition at a total ionic capacity of not less than 2 mmol/g, e.g. between 2 to 5, 3 to 4 mmol/g.

As used herein, the term "total ionic capacity" refers to the total amount of charged sites in the composition which are available for exchange. Total ionic capacity is expressed on a dry weight, wet weight or wet volume basis.

According to some embodiments, the anion exchanger is present at a concentration of 0.5-99% w/v of the total hemostatic composition, optionally at a concentration of 5-15% w/v of the total hemostatic composition, such as, for example, 5%, 6%, 7%, 8%, 9%, 10%, 11%, 12%, 13% 14% or 15%.

According to some embodiments, wherein the anion exchanger is present at a concentration of at least 10% w/v of the total hemostatic composition, a ratio between the anion exchanger and the calcium in the hemostatic composition is in the range of between 1:5 to 1:70. In some embodiments, the ratio is about 1:34.

According to some embodiments, the positively-charged groups consist of a base selected from the group consisting of a strong base (such as one comprising quaternary amino groups), a weak base (such as one comprising an amino group selected from the group consisting of a primary amino group, a secondary amino group, a tertiary amino group) and a combination thereof.

According to some embodiments, the weak base consists of Diethylaminoethyl (DEAE) groups.

According to some embodiments, the positively-charged groups are bound to the matrix e.g. matrix support via a linker present between the matrix support and the positively charged groups.

According to some embodiments, the matrix is selected from the group consisting of a an aliphatic polyester, a polysaccharide, a polypeptide (such as gelatin, bovine serum albumin (BSA) or collagen, or combinations thereof), polyacrylamide, acrylate-copolymer, polystyrene-divinylbenzene, silica and a combination thereof.

According to some embodiments, the matrix is cross-linked, optionally covalently cross-linked. In some such embodiments, the matrix is devoid of ionic cross-linkages.

According to some embodiments, the polysaccharide is selected from the group consisting of cellulose, dextran, agarose, and combinations thereof.

According to some embodiments, the matrix comprises SEPHADEX™ (dextran), SEPHACEL™ (cellulose) or TOYOPEARL™ (hydroxylated methacrylic polymer) or combinations thereof. According to some embodiments, the composition is in a form selected from the group consisting of a slurry, powder, film, patch and liquid. According to some such embodiments, wherein the composition in the form of slurry or liquid, the composition further comprises a pharmaceutically acceptable carrier.

According to some embodiments of the method disclosed herein, applying of the hemostatic composition to the site of bleeding is carried out by applying pressure (e.g. with gauze) on the composition towards a site of bleeding.

According to an aspect of some embodiments of the present invention, there is provided a hemostatic composition comprising an anion exchanger; a calcium salt; and optionally, a pharmaceutically acceptable carrier.

According to some embodiments, the anion exchanger comprises one or more positively-charged groups (also referred to as polycations) bound to a matrix. In some such embodiments, the hemostatic composition is substantially devoid of polyanions.

According to some embodiments, the positively-charged groups are present in the hemostatic composition at a total ionic capacity of not less than 2 mmol/g, e.g. between 2 to 5, 3 to 4 mmol/g According to some embodiments, wherein the anion exchanger is present at a concentration of at least 10% w/v of the total hemostatic composition, a ratio between the anion exchanger and the calcium in the hemostatic composition is in the range of between 1:5 to 1:70. In some embodiments, the ratio is about 1:34.

According to some embodiments, the anion exchanger is present at a concentration of 1-99% w/v of the total hemostatic composition, optionally at a concentration of 5-15% w/v of the total hemostatic composition, such as, for example, 5%, 6%, 7%, 8%, 9%, 10%, 11%, 12%, 13% 14% or 15%.

According to some embodiments, the positively-charged groups are provided by a base selected from the group consisting of a strong base (such as one comprising quaternary amino groups), a weak base (such as one comprising an amino group selected from the group consisting of a primary amino group, a secondary amino group, a tertiary amino group and a combination thereof) and a combination thereof.

According to some embodiments, the weak base comprises Diethylaminoethyl (DEAE) groups.

According to some embodiments, the positively-charged groups are bound to the matrix via a linker present between the matrix support and the positively charged groups.

According to some embodiments, the matrix is selected from the group consisting of a polysaccharide, a polypeptide (such as gelatin, bovine serum albumin (BSA) or collagen, or combinations thereof), polyacrylamide, acrylate-copolymer, polystyrene-divinylbenzene, silica and a combination thereof.

According to some embodiments, the matrix is cross-linked, optionally covalently cross-linked. In some such embodiments, the matrix is devoid of ionic cross-linkages.

According to some embodiments, the polysaccharide is selected from the group consisting of cellulose, dextran, agarose, and combinations thereof.

According to some embodiments, the matrix comprises SEPHADEX™ (dextran), SEPHACEL™ (cellulose) or TOYOPEARL™ (hydroxylated methacrylic polymer) or combinations thereof.

According to some embodiments, the composition is in a form selected from the group consisting of a slurry, powder, film, patch and liquid. According to some such embodiments, wherein the composition in the form of slurry or liquid, the composition further comprises a pharmaceutically acceptable carrier.

According to some embodiments, the salt used herein is a positive divalent cation.

According to some embodiments of the method, composition for use, use or hemostatic composition disclosed herein, calcium is present in the hemostatic composition as a calcium salt such as calcium chloride, calcium acetate, calcium lactate, calcium oxalate, calcium carbonate, calcium gluconate, calcium phosphate, calcium glycerophosphate or combinations thereof. In some embodiments, the calcium salt is calcium chloride, optionally present as a solution, further optionally at a concentration of from 1 to 100 mM. In some such embodiments, calcium present in the hemostatic composition is calcium chloride.

According to some embodiments of the method, composition for use, use or hemostatic composition disclosed herein, the hemostatic composition is substantially devoid of all proteins of the blood clotting cascade.

According to some embodiments, the matrix is devoid of the following polyanionic polymers: alginates and/or hyaluronates.

According to some embodiments, the matrix is devoid of one or more cross-linkable polyanionic polymer selected from the group consisting of polystyrene sulfonate (such as sodium polystyrene sulfonate), a polyacrylate (such as sodium polyacrylate), a polymethacrylate (such as sodium polymethacrylate), a polyvinyl sulphate (such as sodium polyvinyl sulphate), a polyphosphate (such as sodium polyphosphate), Iota carrageenan, Kappa carrageenan, gellan gum, carboxyl methyl cellulose, carboxyl methyl agarose, carboxyl methyl dextran, carboxyl methyl chitin, carboxyl methyl chitosan, a polymer modified with a carboxyl methyl group, an alginate (such as sodium alginate), a polymer containing a plurality of carboxylate groups, a xanthan gum, and combinations thereof.

According to some embodiments, the polymers of the matrix are not modified by the addition of carboxymethyl (CM) groups.

According to some embodiments, a biocompatible polymer is modified with a diethylaminoethyl (DEAE) group to gain cationic functional groups to become a polycationic polymer.

According to some embodiments, the polycationic polymer is selected from the group consisting of a chitosan (such as chitosan chloride), chitin, diethylaminoethyl-dextran, diethylaminoethyl-cellulose, diethylaminoethyl-agarose, diethylaminoethyl-alginate, a polymer modified with a diethylaminoethyl group, a polymer containing a plurality of protonated amino groups, and a polypeptide having an average residue isoelectric point above 7, and combinations thereof. Preferably. the polycationic polymer is diethylaminoethyl-dextran (DEAE-Dextran).

According to some embodiments of the method, composition for use, use or hemostatic composition disclosed herein, the matrix is devoid of alginic acid and of pectic acid.

According to an aspect of some embodiments of the present invention, there is provided a hemostatic composition comprising Diethylaminoethyl (DEAE) bound to a matrix; and a calcium salt.

According to an aspect of some embodiments of the present invention, there is provided a method for the preparation of a hemostatic composition comprising preparing an anion exchanger by covalently binding at least one positively-charged group to a cross-linked matrix; and adding a calcium salt to said anion exchanger.

According to a further aspect of such embodiments of the present invention, there is provided a hemostatic composition obtainable by the method disclosed herein.

According to some embodiments of the method, composition for use, use or hemostatic composition disclosed herein, the hemostatic composition is substantially devoid of all biological hemostats, i.e. devoid of all protein components of the blood clotting cascade, namely Fibrinogen, fibrin, Factor V, Factor Va, Factor VII, Factor VIIa, Factor VIII, Factor VIIIa, Factor IX, Factor IXa, Factor X, Factor Xa, Factor XIa, Factor XI, Factor XII, Factor XIIa, tissue factor (TF), and thrombin, and prothrombinase complex, prothrombin, and vWF., tenase complex, high-molecular-weight kininogen (HMWK), Prekallikrein, kallikrein, thromboplastin.

According to some embodiments of the method, composition for use, use or hemostatic composition disclosed herein, the hemostatic composition is substantially devoid of all proteins of the blood clotting cascade (such as thrombin, prothrombin and fibrinogen).

In some embodiments, the anion exchanger comprises a matrix (also referred to as a "support", "backing", "background", "base beads" or "resin"), which may be solid or semi-solid, optionally in the form of beads to which one or more positively charged group is bound.

Advantageously, the matrix is capable of supporting pressure as typically exerted during surgery when using adjunct materials to stop bleeding without disintegrating.

In some embodiments, the matrix comprises a cross-linked polymer. In some embodiments, the solid or semi-solid matrix material does not dissolve or disintegrate until hemostasis is achieved (at least 1 minute from application of the hemostatic composition).

According to some embodiments, the polymer from which the matrix is formed is insoluble in water, and is preferably porous, having an exclusion limit of at least 20K Da.

According to some embodiments, the matrix does not disintegrate when subjected to manual physical compression.

As used herein, the term "positively charged groups" refers to a molecule comprising chemical groups which carries a positive charge at a pH range of 2.0 to 10 such as ammonium, alkyl ammonium, dialkylammonium, trialkyl ammonium, quaternary ammonium, diethylaminoethyl (DEAE), dimethylaminoethyl (DMAE), triethylaminoethyl, trimethylaminoethyl, alkyl groups, amino functional groups (e.g. $NR_2H^+$), diethyl-(2-hydroxypropyl) aminoethyl, trimethylamino-hydroxypropyl, and a combination thereof.

In one embodiment, the ion exchanger has multiple pKa values, ranging from 6 to 14. In a further embodiment, the ion exchanger has a single pKa value above 9.

According to some embodiments, the anion exchanger comprises DEAE bound to any matrix known to have hemostatic properties, to increase the hemostatic efficacy of the matrix. Examples of suitable matrixes include, without limitation, gelatin, cellulose, collagen, and starch.

According to some embodiments, the hemostatic composition comprises a blend of at least an anion exchanger and calcium. The term "blend" is intended to refer to any form of a mixture, homogenous or non-homogenous, of at least the anion exchanger and the calcium. The blend may optionally further include other ingredients.

According to some embodiments, the blend is substantially free or devoid of any protein component of the blood clotting cascade (i.e. such components are present in the composition at a concentration of less than 0.1% w/w of the total composition), e.g. the blend may be substantially free or devoid of thrombin and fibrinogen.

According to some embodiments, the blend is a slurry, powder or liquid blend.

According to some embodiments, the blend is provided in a frozen state, such that prior to use, the product is thawed and brought to room temperature (i.e. in the range of 15-40° C.), wherein the blend is in its usable state.

According to some embodiments, the composition disclosed herein stops bleeding of a wound within 1 minute.

As used herein, the term "hemostat" or "hemostatic composition" refers to a material or composition which functions by causing blood to clot i.e. induces hemostasis. Typically, a hemostat increases blood coagulation.

In one embodiment, the term "induces hemostasis" with regard to a composition refers to a composition which causes blood to clot by activation of clotting factors, such as prothrombin, resulting in cessation of bleeding or reduction of bleeding intensity.

As used herein, the term "stops bleeding" or "cessation of bleeding" with regard to a composition refers to a composition which, when applied to the site of a wound, results in no bleeding e.g. on a scale of 0 (no bleeding) to 5 as described in the MATERIALS AND METHODS section below.

As used herein, the term "reduction in bleeding intensity" (also referred to herein as "hemostatic efficacy") refers to the difference between the Initial Bleeding Intensity and the Post-Application Bleeding Intensity.

As used herein, the term "Initial Bleeding Intensity" refers to the intensity of bleeding as evaluated immediately following formation of a wound and prior to application of a composition, e.g. on a scale of 0 to 5 as described in the MATERIALS AND METHODS section below.

As used herein, the term "Post-Application Bleeding Intensity" for a specified compression time refers to the intensity of bleeding as evaluated following application of a composition and after the compression time e.g. on a scale of 0 to 5 as described in the MATERIALS AND METHODS section below.

The hemostatic efficacy of the composition can be evaluated in terms of the compression time when applied to a bleeding wound.

As used herein, the term "compression time" refers to the time for which manual compression is applied to a bleeding wound following application of a composition. Typically, this force equals the strength usually exerted by a surgeon upon usage of adjunct products to achieve hemostasis. In some embodiments, wherein no compression is applied, the compression time is referred to as 0 seconds.

In some embodiments, the compression time is about 8 to 12 minutes. In some embodiments, in problematic bleeding, the compression time is about 5 minutes. In some embodiments, in bleeding encountered in a general surgical procedure, the compression time is about 1 to 2 minutes. "Problematic bleeding" is defined as Class III hemorrhage and above according to WHO Classification. Typically, Class III Hemorrhage involves loss of 30-40% of circulating blood volume. Typical symptoms include: a drop in the patient's blood pressure, increase of heart rate, peripheral hypoperfusion (shock).

Without wishing to be bound by any one theory the Inventors hypothesize that when a composition as disclosed herein is applied to a bleeding wound or site, thrombin is generated in-situ. Surprisingly, this in-situ thrombin generation was found to occur to a sufficient extent and with sufficient speed to achieve hemostasis.

Advantageously, the presence of a physical matrix enables the hemostatic composition to be easily applied to the site of bleeding, optionally with compression. Furthermore, the matrix itself may contribute to coagulation by entrapping platelets, similar to oxidized regenerated cellulose (ORC).

As shown in the Examples section below, it was found that a matrix is a prerequisite for the hemostatic capabilities of a positively charged functional group such as DEAE. Typically, the matrix has to be of such a nature that it does not dissolve upon initial contact with liquids and maintains its integrity until hemostasis is achieved, for example, for at least 1 minute, and allows the aggregation of blood proteins to concentrate locally at the wound site thus allowing initiation of the coagulation cascade. Advantageously, the matrix is stable under pressure usually exerted by a surgeon during general surgery to achieve hemostasis. Advantageously, the nature of the matrix is such that it distributes on and/or within the wound following application, optionally with the use of compression.

It was found according to the invention that different Sephadex types and commercial gelatin hemostat, failed to stop bleeding (in a liver bleeding model), i.e. no reduction in bleeding intensity was observed.

The different Sephadex types when including the same base polymer, i.e. cross-linked dextran provided as powders, from which slurries were prepared, surprisingly reduced the bleeding.

Moreover, following the application of DEAE Sephadex, the spleen was manually manipulated by folding the organ from both sides and no re-bleeding occurred.

It was found that while commercial gelatin hemostat failed to stop the bleeding after a compression time of 60 seconds, DEAE SEPHADEX™ A-50 10% (w/v) successfully stopped the bleeding, even following a short compression time of 30 seconds. It was also found that a composition comprising an anion exchanger, such as DEAE bound to a matrix, together with a calcium salt, lead to complete hemostasis.

These compositions substantially lead to complete hemostasis regardless of the specific matrix used.

It was also found that a composition comprising an anion exchanger, such as DEAE bound to a matrix, such as SEPHADEX™, SEPHACEL™ and TOYOPEARL™ (dextran, cellulose and hydroxylated methacrylic polymer, respectively) together with a calcium salt, lead to complete hemostasis.

More particularly it was found that DEAE Sephadex in $CaCl_2$ was able to cease bleeding after 60, and 30 seconds of compression.

It was found that DEAE SEPHADEX™ A-50 (8% w/v) application could be used, without compression, to reduce bleeding intensity.

The hemostatic capabilities of a composition comprising DEAE Sephadex (such as DEAE SEPHADEX™ A-50) and a calcium salt were found to exhibit similar efficacy to that of commercial gelatin hemostat with thrombin, e.g. when using the same compression time (such as 30 seconds or 10 seconds of compression). However, the hemostatic capability of a hemostat based on an anion exchanger comprising DEAE bound to a matrix, and a calcium salt, was substantially superior to that of commercial gelatin hemostat in the absence of a biologically active component, such as thrombin.

It was found according to the invention that a composition comprising DEAE Sephadex prepared with NaCl, but lacking a calcium salt did no reduce bleeding intensity.

The results show that use of a composition comprising DEAE groups bound to a matrix in presence of a calcium salt effectively achieved hemostasis.

The results also showed that compression time of 30 and 60 seconds following DEAE Sephadex application in the presence of calcium salt resulted in complete hemostasis.

Time to hemostasis (TTH) of normal plasma in the presence of calcium (e.g. as measured by clotting assay) is about 200 seconds. Whereas TTH of normal plasma in the presence of calcium and an anion exchanger, according to the invention, is in the range of about 10 to 180 seconds, such as in the range of about 10 to 60 seconds, in the range of about 10 to 30 seconds, in the range of about 15 to 60 seconds, in the range of about 15 to 30 seconds, and in the range of about 30 to 60 seconds. In one embodiment, the TTH is about 30 seconds.

In accordance with the invention it was shown that an anion exchanger such as DEAE bound to a matrix together with a calcium salt provided complete hemostasis. This result was obtained regardless of the matrix used. The results are comparable to those obtained when using a commercial hemostat such as gelatin together with thrombin.

It was found that QAE SEPHADEX™ together with a calcium salt reduced bleeding.

A composition devoid of a calcium salt and/or a matrix had no effect on the bleeding intensity.

These results with DEAE and QAE, suggest that a composition comprising an anion exchanger bound to a matrix and including a calcium salt is effective as a hemostat.

The hemostatic capabilities of DEAE bound to cross-linked polymer in the presence of a calcium salt was further corroborated in a more challenging model of problematic bleeding, modified from that disclosed by Holcomb J B, Pusateri A E, Harris R A, et al. (Effect of dry fibrin sealant dressings versus gauze packing on blood loss in grade V liver injuries in resuscitated swine. J Trauma. 1999; 46:49-58), which is incorporated by reference as if fully set forth herein.

It was shown that DEAE bound to a cross-linked matrix according to the invention was successful in achieving complete hemostasis in-vivo in heparinized porcine spleen circular punch model while DEAE not bound to a matrix failed to decrease the bleeding intensity.

The density (i.e. presence) of positively charged groups which are bound to a matrix as disclosed herein are shown to be of importance in order to achieve hemostasis. Charges on a matrix may advantageously be present at a density which is sufficient to achieve hemostasis according to the invention.

It was found according to the invention that not all positive charges evaluated provided the same level of hemostatic efficacy. Therefore, in order to evaluate the charge density and the type of charge, an analysis can be carried out to ensure that an optimal density range is present.

For example, the synthesized matrix can be monomerized, such as by acid hydrolysis, and applied to an analytical instrument (e.g. High-Pressure Liquid Chromatography, Gas Chromatography), capable of separating the monomers based on the different charges they carry. This way an analysis can be performed to evaluate the charge density on a certain molecule.

EXAMPLES

Materials and Methods

TABLE 1

| Materials | | |
|---|---|---|
| Composition | Manufacturer | Description and Preparation |
| SEPHADEX ™ G-50 Medium | GE healthcare Cat. # 17-0043-01 | Matrix: Cross-linked dextran. Particle Size (dry): 50 μm-150 μm. Supplied as a powder and prepared as a slurry (a flowable material) for application by adding 20 mM $CaCl_2$ solution to the powder. |
| SEPHADEX ™ G-75 Superfine | GE healthcare Cat. # 17-0051-01 | Matrix: Cross-linked dextran. Particle Size (dry): 10 μm-40 μm. Supplied as a powder and prepared as a slurry for application by adding 20 mM $CaCl_2$ solution to the powder. |
| DEAE SEPHADEX ™ A-50 | GE healthcare Cat. # 17-0180-01 | Matrix: Cross-linked dextran. Particle Size (dry): 40 μm-120 μm. Ligand (cation group): diethylaminoethyl (DEAE). |

TABLE 1-continued

Materials

| Composition | Manufacturer | Description and Preparation |
|---|---|---|
| DEAE SEPHACEL ™ | GE healthcare Cat. # 17-0500-01 | Supplied as a powder and prepared as a slurry for application by adding 20 mM $CaCl_2$ or NaCl solutions to the powder. Matrix: Beaded cellulose. Particle Size: 40 μm-160 μm. Ligand: DEAE. Supplied as slurry in 24% ethanol (v/v). The slurry was decanted by leaving the slurry for 40 minutes at room temperature (20° C.-25° C.) in order to allow the particles to settle, then the supernatant was removed and replaced by 20 mM $CaCl_2$ solution. The procedure was repeated 3 times. In the next step, the slurry was placed on a paper for drying (for 1-2 minutes) to obtain a slurry for application. |
| TOYOPEARL DEAE-650M ™ | TOSOH Cat. # 0043201 | Matrix: Hydroxylated methacrylic beads. Particle Size (mean): 65 μm. Ligand: DEAE. Supplied as slurry in 20% ethanol (v/v). Prepared as powder for application by drying the slurry for 12 hours in a vacuum oven at 25° C., the resulting powder was mixed with 10% (w/w) $CaCl_2$ (added as a salt). |
| SP SEPHADEX ™ C-50 | GE healthcare Cat. # 17-0240-01 | Matrix: Cross-linked dextran. Particle Size Dry: 40 μm-120 μm. Ligand (anion group): Sulphopropyl (SP) Supplied as a powder and prepared as a slurry for application by adding 20 mM $CaCl_2$ solution to the powder. |
| QAE SEPHADEX ™ | GE healthcare Cat. # 17-0200-01 | Matrix: Cross-linked dextran. Particle Size (dry): 40 μm-120 μm. Ligand (cation group): Diethyl-(2-hydroxy-propyl) aminoethyl (QAE) Supplied as a powder and prepared as slurry for application by adding 20 mM $CaCl_2$ solution to the powder. |
| 20 mM $CaCl_2$ solution | Sigma Cat. # 21097 | 0.294 g salt dissolved in 100 mL Purified Water (PW) to prepare 20 mM solution. |
| Pure DEAE | Sigma Cat. # 471321 | Colorless liquid Purity (GC) > 99.50% |
| DEAE with calcium | | Prepared by mixing 2 ml DEAE (Sigma; Cat. # 471321) with 2 ml 40 mM $CaCl_2$ solution to provide calcium ions at a final concentration of 20 mM |
| Commercial gelatin hemostat | | Slurry, prepared for application according to the manufacturer's instructions. Gelatin concentration 11% w/v. |
| Commercial gelatin hemostat withthrombin | | Slurry, prepared for application according to the manufacturer's instructions. Gelatin concentration 11% w/v. Thrombin final concentration: 250 IU/ml. Calcium ions final concentration: 10 mM. |
| DEAE Dextran 500 | Pharmacosmos | Matrix: dextran Ligand: DEAE. Average molecular mass Mw: 450,000-550,000. Supplied as powder Prepared as powder for application mixing with 10% (w/w) $CaCl_2$ (added as a salt). |

In-Vivo Circular Punch Model.

The model was based on a model previously described in WO 2012087774 A1, with some modifications. This model evaluates the efficacy of a tested composition in reducing bleeding in-vivo (hemostatic efficacy).

Initially, the organ in which hemostasis was to be studied was exposed and then subjected to a single biopsy punch (4 mm diameter, 2 mm depth in Example 1 and 5; 4 mm diameter, 2 mm depth or 8 mm diameter, 3 mm depth in Example 2, second experiment). The tissue in the punch was removed. The Initial Bleeding Intensity was rated ("initial bleeding") on a scale from 0 to 5 wherein: 0—"No Bleeding"; 1—"Oozing"; 2—"Very Mild Bleeding"; 3—"Mild Bleeding"; 4—"Moderate Bleeding"; 5—"Severe Bleeding".

To evaluate the hemostatic efficacy of each tested composition, approximately 0.5 ml slurry or 100 mg powder (for compositions that were applied as powder) was applied into the bleeding punch wound. Compositions that were applied as a slurry were applied into the wound using a syringe; compositions that were applied as a powder were applied directly onto the wound.

Following application of the compositions, manual compression was optionally applied for a specified time (also referred to herein as "compression time"), using gauze. After the compression, the gauze was removed and Post-Application Bleeding Intensity was evaluated immediately and after a further 1 minute, either qualitatively (yes/no) or quantitatively (using the scale from 0 to 5 as described above).

A tested composition which reduced the bleeding intensity (which started at least at 3) to 1 (Oozing) or 0 (No Bleeding) was considered effective. For qualitative determination, the presence or absence of bleeding was examined visually as well as with a piece of gauze pressed onto the rim of the treated area.

The heparinized biopsy punch model is considered to be a suitable model for evaluating strong hemostasis.

Time to Hemostasis (TTH) was evaluated following application of the composition. Time to Hemostasis (TTH) was evaluated following application of the composition. TTH is defined as the time interval from application of the composition until complete hemostasis (score 0) was observed.

Example 1: The Hemostatic Properties of a Composition Comprising an Anion Exchanger and a Calcium Salt in an In-Vivo Spleen Model Initial evaluation of the hemostatic properties of a composition comprising an anion exchanger and a calcium salt was carried out in an in-vivo heparinized porcine spleen circular punch model as described above, using DEAE covalently bound to Sephadex (DEAE-SEPHADEX™) as the anion exchanger. In this experiment, the punch size was 4 mm diameter, 2 mm depth. A compression time of 30 or 60 seconds was used following application. DEAE SEPHADEX™ A-50 was tested at two concentrations. In this experiment, the Post-Application Bleeding Intensity was evaluated qualitatively.

The following compositions (see elaboration in Table 1 above) were evaluated for their hemostatic efficacy:
1. DEAE SEPHADEX™ A-50, prepared as 10% w/v slurry in 20 mM CaCl$_2$ solution, (0.5 ml contains 50 mg DEAE SEPHADEX™ A-50) (30 seconds compression time);
2. DEAE SEPHADEX™ A-50, prepared as 6.6% w/v slurry in 20 mM CaCl$_2$ solution, (0.5 ml contains 33 mg DEAE SEPHADEX™ A-50) (60 seconds compression time);
3. SEPHADEX™ G-75 Superfine, prepared as 10% w/v slurry in 20 mM CaCl$_2$ solution, (0.5 ml contains 50 mg per SEPHADEX™ G-75 Superfine) (60 seconds compression time);
4. SEPHADEX™ G-50 Medium, prepared as 10% w/v slurry in 20 mM CaCl$_2$ solution, (0.5 ml contains 50 mg SEPHADEX™ G-50 Medium) (60 seconds compression time);
5. Commercial gelatin hemostat prepared as a slurry (0.5 ml contains 55 mg gelatin) (60 seconds compression time).

All four SEPHADEX™ samples comprise the same base polymer, cross-linked dextran. Compositions 1-4 were provided as powders, from which slurries were prepared as described in the Table 1 above. A commercial gelatin flowable hemostat was used as control.

It was found that SEPHADEX™ G-50 Medium, SEPHADEX™ G-75 Superfine and commercial gelatin hemostat, failed to stop the bleeding, i.e. no reduction in bleeding intensity was observed (results not shown).

Surprisingly, DEAE SEPHADEX™ A-50 reduced the bleeding at all tested compression times. Following the application of DEAE SEPHADEX™ A-50, the spleen was manually manipulated by folding the organ from both sides. No re-bleeding occurred at either of the tested concentrations and following the two different compression times (results not shown). Since hemostasis only occurred in the matrix supplemented with DEAE groups it was concluded that the hemostatic effect was due the presence of the DEAE groups.

FIG. 1 shows an exemplary result obtained using DEAE SEPHADEX™ A-50 10% (w/v) and commercial gelatin. As shown in the figure, commercial gelatin hemostat failed to stop the bleeding after a compression time of 60 seconds, whereas DEAE SEPHADEX™ A-50 10% (w/v) successfully stopped the bleeding even following a shorter compression time of 30 seconds.

Example 2: Effect of Compositions Comprising an Anion Exchanger and Calcium on Hemostasis in an In-Vivo Porcine Liver Model In the following Example, the effect on hemostasis of each of the components of a composition comprising an anion exchanger and a calcium salt was evaluated, separately and in combination, using an in-vivo heparinized porcine liver circular punch model, as described above. This experiment identifies which of the components of the composition are required for achieving hemostasis.

The preparation of each composition is described in Table 1 above. Compression time is listed in Table 2 below. In this experiment, the Initial Bleeding Intensity and Post-Application Bleeding Intensity were evaluated according to the 0-5 scale.

The following compositions were evaluated:
1. DEAE SEPHADEX™ A-50, prepared as 8% w/v slurry in 20 mM CaCl$_2$ solution (0.5 ml contains 40 mg DEAE SEPHADEX™ A-50);
2. Commercial gelatin hemostat, prepared as a slurry (0.5 ml contains 55 mg gelatin);
3. Commercial gelatin hemostat with thrombin, prepared as a slurry (0.5 ml contains 55 mg gelatin);
4. SEPHADEX™ G-50 Medium, prepared as 14% w/v slurry in 20 mM CaCl$_2$ solution (0.5 ml contains 70 mg SEPHADEX™ G-50 Medium).
5. DEAE SEPHADEX™ A-50, prepared as 8% w/v slurry in 20 mM NaCl solution (0.5 ml contains 40 mg DEAE SEPHADEX™ A-50);
6. SP SEPHADEX™ C-50, prepared as 8% w/v slurry in 20 mM CaCl$_2$ solution (0.5 ml contains 40 mg SP SEPHADEX™ C-50);
7. QAE SEPHADEX™, prepared as 8% w/v slurry in 20 mM CaCl$_2$ solution (0.5 ml contains 40 mg QAE SEPHADEX™);
8. DEAE SEPHACEL™, prepared as a slurry (100 mg); and
9. TOYOPEARL DEAE-650M™, prepared in powder form (100 mg).

The compression time following the application of each tested composition, and the bleeding intensity results are shown in Table 2. Bleeding Intensity Reduction was calculated by subtracting the Post-Application Bleeding Intensity from the Initial Bleeding Intensity.

TABLE 2

Effect of tested compositions in reduction of bleeding intensity (liver bleeding model)

| Tested Composition | Calcium Salt | Compression time (seconds) | Bleeding Intensity Initial | Bleeding Intensity Post Application | Reduction* |
|---|---|---|---|---|---|
| DEAE SEPHADEX™ A-50 (8% w/v) | + | 60 | 5 | 0 | 5 |
| | + | 30 | 3 | 0 | 3 |
| | + | 10 | 4 | 1 | 3 |
| | + | 0 | 2 | 1 | 1 |

*Calculated by subtracting the Post Application Bleeding Intensity from the Initial Bleeding Intensity.

TABLE 3

Effect of tested compositions in reduction of bleeding intensity (liver bleeding model)

| Tested Composition | Calcium Salt | Bleeding Intensity Initial | Bleeding Intensity Post Application | Reduction* |
|---|---|---|---|---|
| DEAE SEPHACEL™ (100 g slurry) | + | 3 | 0 | 3 |
| TOYOPEARL DEAE-650M™ (100 mg powder) | + | 4 | 0 | 4 |
| QAE SEPHADEX™ (8% w/v) | + | 4 | 3 | 1 |
| DEAE SEPHADEX™ A-50 (8% w/v) with 20 mM NaCl | − | 3 | 3 | 0 |
| SEPHADEX™ G50 (14% w/v) | + | 3 | 3 | 0 |
| SP SEPHADEX™ C-50 (8% w/v) | + | 3 | 3 | 0 |
| Commercial gelatin hemostat with thrombin | + | 3 | 0 | 3 |
| Commercial gelatin hemostat | − | 3 | 3 | 0 |

*Calculated by subtracting the Post Application Bleeding Intensity from the Initial Bleeding Intensity.

In general, it can be seen, that a composition comprising an anion exchanger, such as DEAE bound to a matrix, together with a calcium salt, lead to complete hemostasis (see Table 2 for DEAE SEPHADEX™ A-50, DEAE SEPHACEL™, and TOYOPEARL DEAE-650M™, all containing a calcium salt). These compositions substantially lead to complete hemostasis regardless of the specific matrix used. For example, matrices such as SEPHADEX™, SEPHACEL™ and TOYOPEARL™ (dextran, cellulose and hydroxylated methacrylic polymer, respectively) had a similar effect in reducing the bleeding intensity.

More particularly, DEAE SEPHADEX™ A-50 8% w/v in $CaCl_2$ was able cease bleeding after 60, and 30 seconds of compression. The results also showed DEAE SEPHADEX™ A-50 (8% w/v) application could be used, without compression, to reduce bleeding intensity (Table 2).

The hemostatic capabilities of a composition comprising DEAE SEPHADEX™ A-50 and a calcium salt exhibited similar efficacy to that of commercial gelatin hemostat with thrombin, when using the same compression time (30 seconds), and even with only 10 seconds of compression. However, the hemostatic capability of a hemostat based on an anion exchanger comprising DEAE bound to a matrix, and a calcium salt, was substantially superior to that of commercial gelatin hemostat in the absence of a biologically active component, such as thrombin.

As shown in Table 3, a composition comprising DEAE SEPHADEX™ prepared with NaCl, and lacking a calcium salt produced no reduction in bleeding intensity, such that it can be concluded that the sample was not effective in stopping the bleeding.

When evaluating the impact of the ion exchange group on the hemostatic capability, it was shown that SP SEPHADEX™ containing an anionic group, sulfopropyl (SP) with a calcium salt, did not reduce the bleeding intensity. In other words, a material with a negative (SP) group, instead of a positive (DEAE) group was not effective as a hemostat.

It was further shown that a quaternary aminoethyl, QAE SEPHADEX™ with a calcium salt was able to reduce bleeding intensity.

It was also shown, as in Example 1, that the matrix alone, in the absence of a functional group (SEPHADEX™ G-50 with a calcium salt but without DEAE groups) had no hemostatic efficacy.

The results show that use of a composition comprising DEAE groups bound to a matrix in presence of a calcium salt effectively achieved hemostasis.

The results also showed that compression time of 30 and 60 seconds following DEAE SEPHADEX™ A-50 (8% w/v) application resulted in complete hemostasis and therefore the TTH was defined as 30 seconds.

It was thus shown that an anion exchanger such as DEAE bound to a matrix together with a calcium salt provided complete hemostasis. This result was obtained regardless of the matrix used. The results are comparable to those obtained when using a commercial hemostat such as gelatin with thrombin.

It was found that QAE SEPHADEX™ together with a calcium salt reduced bleeding.

A composition devoid of a calcium salt and/or a matrix had no effect on the bleeding intensity.

These results suggest that a composition comprising an anion exchanger and a calcium salt is effective as a hemostat.

Example 3: Effect of Compositions Comprising an Anion Exchanger and a Calcium Salt on Hemostasis in an In-Vivo Porcine Spleen Model The previous experiment showed that a composition comprising an anion exchanger consisting of DEAE bound to a cross-linked polymer, and a calcium salt, was effective in reducing the bleeding intensity in an in-vivo spleen circular punch model.

In this experiment, the hemostatic activity of the composition was corroborated in another model, in-vivo heparinized porcine spleen circular punch model (carried out as described above). This model was more severe than the previous model with regards to the bleeding intensity. The compression time for all samples was 30 seconds. For samples 1-6, punch size was 4 mm diameter, 2 mm depth. For samples 7-9, punch size was 8 mm diameter and 3 mm depth. Typically, the severity of bleeding increased with the increase in punch size and/or addition of heparin.

The following samples were tested for their hemostatic efficacy:
1. DEAE SEPHADEX™ A-50, prepared as 8% w/v slurry in 20 mM $CaCl_2$ solution (0.5 ml contains 40 mg DEAE SEPHADEX™ A-50);
2. DEAE SEPHADEX™ A-50, prepared as 10% w/v slurry in 20 mM $CaCl_2$ solution (0.5 ml contains 50 mg DEAE SEPHADEX™ A-50), tested in duplicate;

3. Commercial gelatin hemostat, prepared as a slurry (0.5 ml contains 55 mg gelatin);
4. Commercial gelatin hemostat with thrombin, prepared as a slurry (0.5 ml contains 55 mg gelatin);
5. SEPHADEX™ G-50 Medium, prepared as 14% w/v slurry in 20 mM $CaCl_2$ solution (0.5 ml contains 70 mg SEPHADEX™ G-50 Medium);
6. DEAE SEPHADEX™ A-50, prepared as 8% w/v slurry in 20 mM NaCl solution (0.5 ml contains 40 mg DEAE SEPHADEX™ A-50);
7. Pure DEAE;
8. $CaCl_2$ (20 mM); and
9. DEAE with $CaCl_2$.

It was observed that DEAE SEPHADEX™ A-50 8% and 10% w/v in the presence of $CaCl_2$ were able to reduce the bleeding intensity (a reduction of about 2-3 points was observed), with the higher percentage providing better results. In this model, the hemostatic capabilities of DEAE SEPHADEX™ A-50 were superior to those of the commercial gelatin based hemostat with or without thrombin.

As shown for the liver experiment, both SEPHADEX™ G-50 alone and DEAE SEPHADEX™ with a sodium salt failed to reduce the bleeding intensity.

Pure DEAE failed to reduce the bleeding intensity. It was therefore concluded that when DEAE is not bound to a cross-linked polymer, it does not function as an effective hemostat (i.e. no significant bleeding reduction occurred). The addition of a calcium salt did not improve the hemostatic capabilities of DEAE in the absence of a matrix, as can be seen for the composition comprising DEAE with a calcium salt composition (0 points reduction). It was also demonstrated that a calcium salt alone did not possess hemostatic capabilities.

This experiment further supported the previous experiment and showed that the combination of a calcium salt, DEAE groups and a matrix were required for the hemostatic efficacy demonstrated.

Example 4: The Hemostatic Properties of a Solution Comprising an Anion Exchanger and a Calcium Salt in an In-Vivo Porcine Spleen Problematic Bleeding Model In this Example, the hemostatic capabilities of DEAE bound to cross-linked polymer in the presence of a calcium salt was further tested in a more challenging model of problematic bleeding, modified from that disclosed by Holcomb J B, Pusateri A E, Harris R A, et al. (Effect of dry fibrin sealant dressings versus gauze packing on blood loss in grade V liver injuries in resuscitated swine. J Trauma. 1999; 46:49-58), which is incorporated by reference as if fully set forth herein.

Figure 2A:
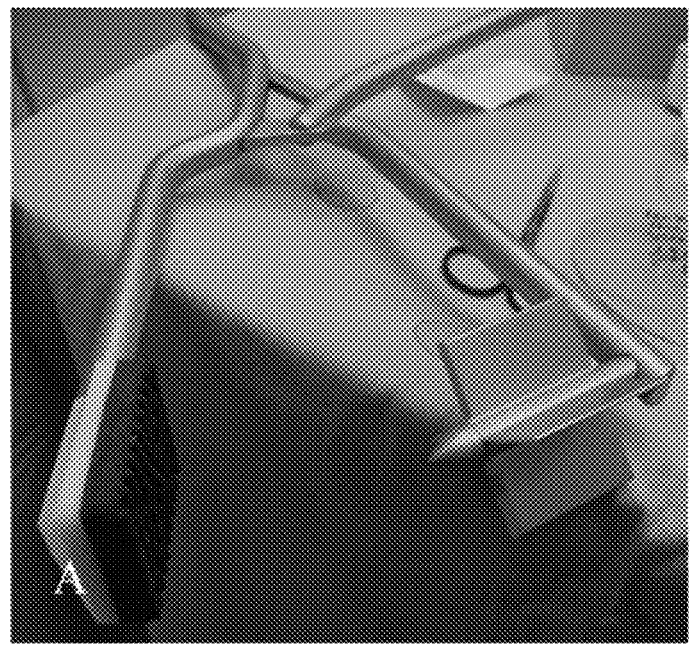
FIG. 2a shows a device used for a Porcine Spleen Problematic Bleeding Model in order to create a "bullet-like" wound.
Figure 2B:
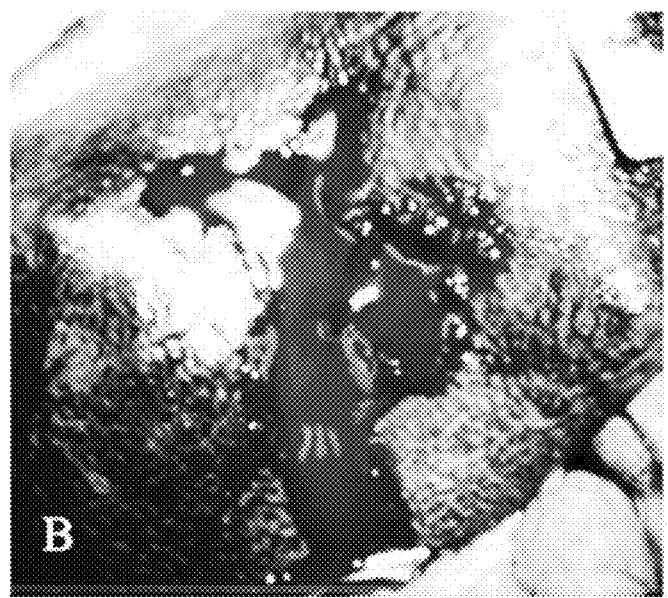
FIG. 2b shows a wound created by the device of FIG. 2a in a porcine spleen. As can be seen in FIG. 2b, the wound results in severe bleeding from the spleen. DEAE SEPHADEX™ A-50 was prepared as a slurry of 10% w/v in 20 mM $CaCl_2$ and applied to the wound. Following the application of the slurry, and compression time of 4 minutes, the Post-Application Bleeding Intensity was evaluated as described for FIG. 1.
Figure 2C:
FIG. 2c shows the bullet-like wound following application of DEAE SEPHADEX™ A-50 and tamponade, which achieved complete hemostasis of the severely bleeding wound.

DEAE SEPHADEX™ A-50 was prepared as 10% w/v slurry in a 25 mM $CaCl_2$ solution. A punch was performed using a dedicated device (see FIG. 2a), resulting in an X shaped wound, where each arm is 5.5 cm long and the center hole is 1.5 cm deep, bullet shaped and 9.5 mm in diameter (FIG. 2b). The wound represented a problematic bleeding (such as bullet injury).

About 20 ml of the tested composition was applied on the wound. Manual compression was applied to the wound site for four minutes. The tested composition stopped the bleeding.

The experiment was carried out in triplicate (two more repetitions) and similar results were obtained.

If in a first trial not enough material was present to achieve complete hemostasis, then additional material was applied and the compression was exerted for an additional three minutes. Complete hemostasis was then achieved.

Example 5: Evaluation of the Matrix Requirement

In the following example, the requirements of the matrix to which DEAE is bound were further evaluated using an in-vivo heparinized porcine spleen circular punch model, as described above. The preparation of the compositions is described in Table 1 above. Compression time was 60 seconds. In this experiment, the Initial Bleeding Intensity and Post-Application Bleeding Intensity were evaluated according to the 0-5 scale.

DEAE Dextran 500 is a polycatonic derivative of Dextran, prepared from dextran of average molecular weight of 500 kD, in which the dextran chains are not cross-linked.

The following compositions were evaluated:
1. DEAE SEPHADEX™ A-50, prepared as 10% w/v slurry in 20 mM $CaCl_2$ solution (0.5 ml contains 40 mg DEAE SEPHADEX™ A-50);
2. DEAE dextran 500, prepared with 10% (w/w) $CaCl_2$ powder (100 mg powder contained 90 mg DEAE dextran and 10 mg $CaCl_2$).

The bleeding intensity results of the different tested compositions are shown in Table 4.

TABLE 4

Effect of tested compositions in reduction of bleeding intensity in a spleen bleeding model

| Tested Composition | Calcium Salt | Bleeding rate | | |
|---|---|---|---|---|
| | | Initial | Post Application | Reduction* |
| DEAE SEPHADEX™ A-50 (10% w/v) | + | 3 | 0 | 3 |
| DEAE Dextran 500 100 mg | + | 3 | 3 | 0 |
| DEAE Dextran 500 100 mg | + | 2 | 3 | 0 |

DEAE bound to a cross-linked matrix was successful in achieving complete hemostasis while DEAE not bound to a matrix failed to decrease the bleeding intensity.

Example 6: Effect of Positive Charged Groups on Hemostasis

The density (i.e. presence) of positively charged groups which are bound to a matrix as disclosed herein are shown to be of importance in order to achieve hemostasis. Charges on a matrix should advantageously be present at a density which is sufficient to achieve hemostasis as defined above.

It was shown in previous examples that not all positive charges evaluated provided the same level of hemostatic efficacy. Therefore, in order to evaluate the charge density and the type of charge, an analysis is carried out to ensure that an optimal density range is present.

To this end the synthesized matrix is monomerized, such as by acid hydrolysis, and applied to an analytical instrument (e.g. High-Pressure Liquid Chromatography, Gas Chromatography), capable of separating the monomers based on the different charges they carry. This way an analysis is performed to evaluate the charge density on a certain molecule.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The invention claimed is:

1. A hemostatic composition comprising:
   an anion exchanger; wherein the anion exchanger comprises one or more positively-charged groups bound to a matrix; wherein said positively-charged groups comprise diethylaminoethyl (DEAE) groups, diethyl-(2-hydroxypropyl)aminoethyl groups, or combinations thereof;
   a calcium salt; and
   optionally, a pharmaceutically acceptable carrier;
   wherein:
   (i) a polyanionic polymer is not present in the hemostatic composition;
   (ii) thrombin is not present in the hemostatic composition;
   (iii) the calcium is present at a concentration of from 1 to 100 mM or the ratio between the anion exchanger and the calcium salt in the composition ranges from 1:5 to 1:70, respectively, by weight
   (iv) the hemostatic composition comprises a homogenous blend of said matrix and calcium, and wherein:
   (v) the hemostatic composition is a blend in the form selected from powder, slurry and liquid.

2. The hemostatic composition according to claim 1, wherein said matrix is cross-linked.

3. The hemostatic composition according to claim 1, wherein the composition is devoid of any protein of the blood clotting cascade.

4. The hemostatic composition according to claim 1, wherein said composition in the form of slurry or liquid and further comprises a pharmaceutically acceptable carrier.

5. A hemostatic composition comprising:
   Diethylaminoethyl (DEAE) bound to a matrix; and a calcium salt;
   wherein:
   (i) a polyanionic polymer is not present in the hemostatic composition;
   (ii) thrombin is not present in the hemostatic composition;
   (iii) the calcium is present at a concentration of from 1 to 100 mM or the ratio between the matrix and the calcium salt in the composition ranges from 1:5 to 1:70, respectively, by weight;
   (iv) the hemostatic composition comprises a homogenous blend of said matrix and calcium, and wherein:
   (v) wherein the hemostatic composition is a blend in the form selected from powder, slurry and liquid.

* * * * *